United States Patent [19]
Verduijn et al.

[11] Patent Number: 6,150,293
[45] Date of Patent: Nov. 21, 2000

[54] PREPARATION OF ZEOLITE BOUND BY MFI STRUCTURE TYPE ZEOLITE AND USE THEREOF

[75] Inventors: Johannes P. Verduijn, deceased, late of Oostvoorne, Netherlands, by Jannetje Maatje van den Berge, executrix; Machteld Maria Mertens, Boortmeerbeek; Wilfried Jozef Mortier, Kessel-lo, both of Belgium

[73] Assignee: Exxon Chemical Patents Inc., Houston, Tex.

[21] Appl. No.: 09/204,736

[22] Filed: Dec. 3, 1998

Related U.S. Application Data

[60] Provisional application No. 60/067,417, Dec. 3, 1997.

[51] Int. Cl.⁷ .............................. B01J 29/80; B01J 29/40
[52] U.S. Cl. ............................... 502/67; 502/63; 502/64; 502/71; 502/77
[58] Field of Search ................................. 502/63, 64, 67, 502/71, 77

[56] References Cited

U.S. PATENT DOCUMENTS

| | | | |
|---|---|---|---|
| 5,460,796 | 10/1995 | Verduijn | 423/700 |
| 5,665,325 | 9/1997 | Verduijn | 423/709 |
| 5,672,331 | 9/1997 | Verduijn | 423/702 |
| 5,993,642 | 11/1999 | Mohr et al. | 208/46 |
| 5,994,603 | 11/1999 | Mohr et al. | 585/467 |
| 5,998,686 | 12/1999 | Clem et al. | 585/415 |
| 6,008,425 | 12/1999 | Morh et al. | 585/481 |

FOREIGN PATENT DOCUMENTS

| | | | |
|---|---|---|---|
| 0599117 | 1/1994 | European Pat. Off. | B01J 29/06 |
| 1 511 892 | 5/1978 | United Kingdom . | |
| WO9212928 | 8/1992 | WIPO | C01B 33/34 |
| WO9308125 | 4/1993 | WIPO | C01B 33/334 |
| WO9405597 | 3/1994 | WIPO | C01B 33/26 |
| WO9616004 | 5/1996 | WIPO | C07C 2/66 |
| WO9703019 | 1/1997 | WIPO | C01B 39/04 |
| WO9745198 | 12/1997 | WIPO | B01J 29/80 |

*Primary Examiner*—Tom Dunn
*Attorney, Agent, or Firm*—Edward F. Sherer

[57] ABSTRACT

The preparation of zeolite bound zeolite comprising zeolite core crystals other than MFI structure zeolite which are bound by MFI structure type zeolite and the use of the zeolite bound by MFI structure type zeolite prepared by the process as an adsorbent or as a catalyst for hydrocarbon conversion. The zeolite bound zeolite is produced by including seed crystals of MFI structure type zeolite into the silica bound aggregate forming mixture and then converting the silica binder of the aggregate to the MFI binder crystals. The resulting zeolite bound zeolite has good strength and integrity.

21 Claims, No Drawings

6,150,293

1

PREPARATION OF ZEOLITE BOUND BY MFI STRUCTURE TYPE ZEOLITE AND USE THEREOF

This application claims priority to U.S. Provisional patent application Ser. No. 60/067,417, filed Dec. 3, 1997.

FIELD OF THE INVENTION

This invention relates to a process for preparing zeolite bound by MFI structure type zeolite and the use of the zeolite bound by MFI structure type zeolite prepared by the process as an adsorbent or as a catalyst for hydrocarbon conversion.

BACKGROUND OF THE INVENTION

Zeolites are comprised of a lattice of silica and optionally alumina combined with exchangeable cations such as alkali or alkaline earth metal ions. Although the term "zeolites" includes materials containing silica and optionally alumina, it is recognized that the silica and alumina portions may be replaced in whole or in part with other oxides. For example, germanium oxide, tin oxide, phosphorous oxide, and mixtures thereof can replace the silica portion. Boron oxide, iron oxide, gallium oxide, indium oxide, and mixtures thereof can replace the alumina portion. Accordingly, the terms "zeolite", "zeolites" and "zeolite material", as used herein, shall mean not only materials containing silicon and, optionally, aluminum atoms in the crystalline lattice structure thereof, but also materials which contain suitable replacement atoms for such silicon and aluminum, such as gallosilicates, silicoaluminophosphates (SAPO) and aluminophosphates (ALPO). The term "aluminosilicate zeolite", as used herein, shall mean zeolite materials consisting essentially of silicon and aluminum atoms in the crystalline lattice structure thereof.

Synthetic zeolites are normally prepared by the crystallization of zeolites from a supersaturated synthesis mixture. The resulting crystalline product is then dried and calcined to produce a zeolite powder. Although the zeolite powder has good adsorptive properties, its practical applications are severely limited because it is difficult to operate fixed beds with zeolite powder. Therefore, prior to using the powder in commercial processes, the zeolite crystals are usually bound.

The zeolite powder is typically bound by forming a zeolite aggregate such as a pill, sphere, or extrudate. The extrudate is usually formed by extruding the zeolite in the presence of a non-zeolitic binder and drying and calcining the resulting extrudate. The binder materials used are resistant to the temperatures and other conditions, e.g., mechanical attrition, which occur in various hydrocarbon conversion processes. Examples of binder materials include amorphous materials such as alumina, silica, titania, and various types of clays. It is generally necessary that the zeolite be resistant to mechanical attrition, that is, the formation of fines, which are small particles, e.g., particles having a size of less than 20 microns.

Although such bound zeolite aggregates have much better mechanical strength than the zeolite powder, when such a bound zeolite is used for hydrocarbon conversion, the performance of the zeolite catalyst, e.g., activity, selectivity, activity maintenance, or combinations thereof, can be reduced because of the binder. For instance, since the binder is typically present in an amount of up to about 50 wt. % of zeolite, the binder dilutes the adsorption properties of the zeolite aggregate. In addition, since the bound zeolite is prepared by extruding or otherwise forming the zeolite with the binder and subsequently drying and calcining the extrudate, the amorphous binder can penetrate the pores of the zeolite or otherwise block access to the pores of the zeolite, or slow the rate of mass transfer to the pores of the zeolite which can reduce the effectiveness of the zeolite when used in hydrocarbon conversion. Furthermore, when the bound zeolite is used in hydrocarbon conversion, the binder may affect the chemical reactions that are taking place within the zeolite and also may itself catalyze undesirable reactions, which can result in the formation of undesirable products.

For certain hydrocarbon conversion processes, it is sometimes desirable that the zeolite catalysts be tailored to maximize their performance. One method for tailoring zeolite catalysts is to bind zeolite core crystals with binder crystals of a zeolite having a structure type that is different from the core crystals. Such catalysts are disclosed in PCT Publication WO PCT/US97/45198.

Zeolite catalysts comprising zeolite core crystals which are bound together by binder crystals of a zeolite having a different structure type different from the core crystals can be bifunctional, i.e., capable of performing two or more functions. For example, the catalysts can induce separate reactions (the zeolite core crystals and zeolite binder crystals each inducing reactions). Also, the zeolite binder crystals can reduce the amount of reactions taking place on the surface of the zeolite core crystals. Still further, the zeolite binder crystals can reduce accessibility of reactants to the surface of the zeolite core crystals by selectively sieving molecules in the hydrocarbon feedstream based on their size or shape to prevent undesirable molecules present in the feedstream from entering the catalytic phase of the zeolite core crystals and/or selectively sieve desired molecules based on their size or shape in order to prevent undesirable molecules from exiting the catalyst phase of the core crystals.

One procedure for making zeolite-bound zeolite involves converting the silica present in the silica binder of a silica-bound zeolite aggregate to a zeolite binder. The procedure involves aging the silica bound aggregate for sufficient time in an aqueous alkaline solution. When such a procedure is used to produce MFI-bound zeolite having zeolite core crystals with structure type other than MFI, certain problems can arise which result in the MFI-bound zeolite having less than desirable strength and integrity. For instance, if the alkalinity of the aging solution is too high or the time needed for conversion of the silica binder is too long, the core crystals and/or silica-bound aggregate can lose their integrity. This can result in the MFI-bound zeolite having less than acceptable strength and/or integrity.

The present invention provides a process for preparing zeolite (other than MFI) core crystals that are bound by MFI structure type zeolite which overcomes or at least mitigates the above described problems. The zeolite bound zeolite made by the process finds particular application as an adsorbent or as a catalyst in hydrocarbon conversion.

SUMMARY OF THE INVENTION

It has been discovered that if seed crystals of a MFI structure type zeolite are included in a silica bound aggregate forming mixture containing zeolite having a structure type other than MFI, the silica binder of the silica bound aggregates can be converted in an aqueous alkaline mixture optionally containing an organic template to MFI-bound zeolite having good strength and integrity. The presence of the seed crystals allows the silica conversion to take place under conditions that are less severe, e.g., lower alkalinity, shorter crystallization time, and lower temperatures, than would be required if seeds were not present. Also, the presence of the seeds enables the conversion to take in less time than would be needed if seeds were not present.

The zeolite bound zeolite catalyst produced by the process finds particular application in hydrocarbon conversion processes. Examples of preferred processes include hydrocarbon conversion process where reduced non-selective acidity is important for reaction selectivity and/or the maintenance of catalyst activity, such as alkylation, dealkylation, disproportionation, and transalkylation reactions. The lower alkalinity conditions and reduced time for the silica conversion results in substantial reduction in the core crystal and aggregate integrity.

DETAILED DESCRIPTION OF THE INVENTION

The process for preparing the MFI-bound zeolite (other than MFI) preferably comprises the following steps:

(a) Forming an extrudable mass comprising core crystals of a zeolite other than MFI, silica, water, an effective amount of seeds of MFI structure type zeolite, and optionally an extrusion aid;

(b) Extruding the extrudable mass to form silica-bound zeolite aggregates; and (c) Aging the silica bound zeolite aggregate in an aqueous ionic solution containing sufficient hydroxy ions and optionally an organic template at sufficient temperature to cause the silica binder to be converted to the MFI binder crystals.

The seed crystals will have a MFI structure type and can be in powdered form. Preferably, the seeds will have an average diameter of 200 nm or less. More preferably, the seed crystals will comprise crystals or agglomerates of a MFI structure type zeolite having an average largest dimension of 100 nm or less and are capable of forming a colloidal suspension. The use of seed crystals having an average largest dimension of 100 nm or less and capable of forming a colloidal suspension is especially beneficial for carrying out the process of the present invention as lesser amounts of seeds will be required and the seed crystals will not interfere with the composition of the MFI binder crystals. The manufacture of seed crystals having an average diameter of 200 nm or less is described in PCT Publications WO 93/08125, WO 97/03019, and WO 94/05597 and U.S. Pat. No. 5,672, 331 which are hereby incorporated by reference in their entirety.

The silica binder used in preparing the silica-bound zeolite aggregate may be commercially available silica. The silica does not need to contain significant amounts of alumina, and can even contain less than 2000 ppm of alumina.

The seed crystals can be added to the silica-bound aggregate forming mixture at any time prior to extruding the mixture. For example, the seed crystals can be added to the silica or zeolite crystals used in the forming mixture or can be added directly to the forming mixture . The seed crystals will be present in an effective amount which will usually be an amount in the range of from about 0.01 to about 2% by weight based on the dry weight of the silica bound extrudate.

The zeolite aggregate, which is sometimes referred to herein as an extrudate, used in the present invention will usually be prepared by first forming the zeolite core crystals. Next the crystals are washed, dried, and optionally calcined to produce zeolite powder. The zeolite powder can then be mixed with a silica sol together with the seed crystals and optionally an extrusion aid to form a thick, smooth paste. The paste is then extruded to form the silica-bound extrudate, which is dried and optionally calcined.

When carrying out the process of the present invention the zeolite extrudate is usually aged at elevated temperature. A suitable aging temperature may range from 95° to 200° C. Generally the zeolite extrudate is aged at temperatures from 130° C. to 170° C., preferably 145° C. to 155° C., most preferably around 150° C.

The time during which the extrudate is aged is usually from 10 to 80 hours.

The aqueous ionic solution in which the silica-bound aggregate is aged will contain reduced amounts of hydroxy ions as higher amounts can result in substantial reduction in the core crystal and aggregate integrity. The amount of hydroxy ions present in present in the aqueous ionic mixture will usually be a molar ratio of (OH—):($SiO_2$) of less than 0.20, preferably less than about 0.16, or even less depending on the composition of the MFI binder crystals.

The zeolites that can be bound by the process of the present invention include any of the naturally occurring or synthetic crystalline zeolites. Examples of these zeolites include large pore zeolites, intermediate pore zeolites, and small pore zeolites. These zeolites and their isotypes are described in "Atlas of Zeolite Structure Types", eds. W. H. Meiser, D. H. Olson and Ch. Baerlocher, Elsevier, Fourth Edition, 1996, which is hereby incorporated by reference. A large pore zeolite generally has a pore size of at least about 7 Å and includes LTL, MAZ, MEI, FAU, EMT, OFF, BEA, and MOR structure type zeolites (IUPAC Commission of Zeolite Nomenclature). Examples of large pore zeolites, include mazzite, offretite, zeolite L, zeolite Y, zeolite X, omega, Beta, ZSM-3, ZSM-4, ZSM-18, ZSM-20, and MCM-22. A intermediate pore size zeolite generally has a pore size from about 5 Å to about 7 Å and includes, for example, MFI, MEL, MTW, EUO, MTT, MFS, HEU, FER, and TON structure type zeolites (IUPAC Commission of Zeolite Nomenclature). Examples of intermediate pore size zeolites, include ZSM-5, ZSM-12, ZSM-22, ZSM-23, ZSM-34, ZSM-35, ZSM-38, ZSM-48, ZSM-50, ZSM-57, silicalite, and silicalite 2. A small pore size zeolite has a pore size from about 3 Å to about 5.0 Å and includes, for example, CHA, ERI, FKI, LEV, and LTA structure type zeolites (IUPAC Commission of Zeolite Nomenclature). Examples of small pore zeolites include ZK-4, SAPO-34, SAPO-35, ZK-14, ZK-21, ZK-22, ZK-5, ZK-20, zeolite A, erionite, chabazite, zeolite T, gemlinite, and clinoptilolite. The preferred zeolites will have pore apertures consisting of about 8 to about 10 membered ring structures.

The zeolite bound zeolites generally will not contain significant amounts of non-zeolite binder, e.g., the zeolite bound zeolite produced by the process of the present invention usually will contain less than 10 percent by weight, based on the weight of the zeolites, of non-zeolitic binder, more preferably will contain less than 5 percent by weight, and, most preferably, the catalyst will be substantially free of non-zeolitic binder. The binding crystals can bind the core crystals by adhering to the surface of the core crystals thereby forming a matrix or bridge structure, which also holds the core crystals together. The zeolite binder can bind the core crystals by growing together so as to form a coating or partial coating on the larger core crystals. Preferably, the zeolite binding crystals bind the core crystals by intergrowing to form an attrition resistant over-growth over the core crystals.

The term "average particle size" as used herein means the arithmetic average of the diameter distribution of the crystals on a volume basis.

The average particle size of the core crystals will usually be from about 0.1 to about 15 microns. In some applications, it will preferably the average particle size be from 1 to about 6 microns. In other applications such as the cracking of hydrocarbons, the average particle size of the core crystals will be smaller, e.g., from about 0.1 to about 3.0 microns.

The zeolites of the core crystals will usually comprise compositions having the following molar relationship:

$$X_2O_3:(n) YO_2,$$

wherein X is a trivalent element, such as titanium, boron, aluminum, iron, and/or gallium, Y is a tetravalent element such as silicon, tin, and/or germanium, and n has a value of at least 2, said value being dependent upon the particular type of zeolite and the trivalent element present in the zeolite.

When zeolite of the core crystals has an intermediate pore size, the zeolite preferably comprises a composition having the following molar relationship:

$$X_2O_3:(n) YO_2,$$

wherein X is a trivalent element, such as aluminum, and/or gallium, Y is a tetravalent element such as silicon, tin, and/or germanium; and n has a value greater than 10, said value being dependent upon the particular type of zeolite and the trivalent element present in the zeolite.

When the zeolite of the core crystals is a gallium silicate intermediate pore size zeolite, the zeolite preferably comprises a composition having the following molar relationship:

$$Ga_2O_3:ySiO_2$$

wherein y is between about 24 and about 500. The zeolite framework may contain only gallium and silicon atoms or may also contain a combination of gallium, aluminum, and silicon. When the zeolite of the binder crystals is a gallium silicate, y is usually greater than 50, e.g., 100, 200, etc.

When the zeolite of the core crystals is an aluminosilicate zeolite, the silica to alumina mole ratio will usually depend upon the structure type of the binder zeolite and the particular hydrocarbon process in which the catalyst system is utilized and is therefore not limited to any particular ratio. Generally, however, and depending on the structure type of the zeolite, the zeolite will have a silica to alumina mole ratio of at least 2:1 and in some instances from 4:1 to about 7:1. For a number of zeolites, especially intermediate pore size zeolites, the silica to alumina mole ratio will be in the range of from about 10:1 to about 1,000:1. When the zeolite bound zeolite is utilized in acid catalyzed reactions such as cracking, the manufacture of paraxylene and benzene by the disproportionation of toluene, the alkylation of benzene or the like, the zeolite of the core crystals will be acidic and will preferably, when it is an intermediate pore size zeolite, have higher silica to alumina mole ratios, e.g., 20:1 to about 200:1. If the zeolite bound zeolites is utilized in a process where acid catalyzed reactions may not desired, such as a the reforming of naphtha, the zeolite of the core crystals will preferably exhibit reduced acid activity.

The MFI structure type zeolite binder crystals and seed crystals will generally be a composition having the following molar relationship:

$$X_2O_3:(n) YO_2,$$

wherein X is a trivalent element, such as aluminum, and/or gallium, Y is a tetravalent element such as silicon, tin, and/or germanium; and n has a value greater than 10, e.g., 100, 300, 1000, etc.

When the zeolite of the binder crystals or seed crystals are aluminosilicate zeolite, the silica to alumina mole ratio of the zeolite will usually depend upon particular hydrocarbon process in which the zeolite bound zeolite is utilized and is therefore not limited to any particular ratio. In applications where low acidity is desired, the zeolite will usually have a silica to alumina mole ratio greater than the silica to alumina mole ratio of the zeolite of the core crystals, and more preferably is greater than 200:1. The zeolite can also have higher silica to alumina mole ratios, e.g., 300:1, 500:1, 1,000:1, etc. In certain applications, the zeolite binder or seed crystals may be a Silicalite i.e., the zeolite is a MFI structure type substantially free of alumina. In applications where higher acidity is desired, the zeolite can have a silica to alumina mole ratio of less than 100 including less than 50. The zeolite can have higher acidity, lower acidity, or the same acidity as the zeolite of the core crystals.

The binder is usually present in the zeolite bound zeolite in an amount in the range of from about 10 to about 60% by weight based on the weight of the core crystals and, more preferably from about 20 to about 50% by weight.

As previously stated, the first step of the process usually involves the synthesis of the zeolite core crystals. Processes for preparing the zeolite core crystals are known to persons skilled in the art. Because of the low alkalinity silica conversion conditions which will protect the core crystals from deteriorating during conversion, it is contemplated that any of the previously described zeolites can be bound by the MFI binder crystals using the process of the present invention.

In the second step, a silica-bound zeolite aggregate is prepared by forming a mixture comprising the core crystals, a silica gel or sol, water, an effective amount of seed crystals, and optionally an extrusion aid, until a homogeneous composition in the form of an extrudable paste develops. Optionally, the silica can contain alumina. The silica binder used in preparing the silica bound zeolite aggregate is preferably a silica sol and can contain various amounts of trivalent elements, e.g., aluminum, gallium, boron, iron, zinc, or mixtures thereof. The amount of silica used is such that the content of the zeolite in the dried extrudate at this stage will range from about 40 to 90% by weight more preferably from about 50 to about 80% by weight, with the balance being primarily silica, e.g. about 20 to 50% by weight silica.

The resulting paste can then be molded, e.g., extruded, and cut into small strands, e.g., approximately 2 mm diameter extrudates, which are dried at 100° C. to 150° C. for a period of 4–12 hours and then are calcined in air at a temperature of from about 400° C. to 550° C. for a period of from about 1 to 10 hours.

Optionally, the silica-bound aggregate can be made into very small particles, which have application in fluid bed processes such as catalytic cracking. This preferably involves mixing the zeolite with a silica and seed crystals so that an aqueous solution of zeolite and silica binder is formed which can be sprayed dried to result in small fluidizible silica-bound aggregate particles. Procedures for preparing such aggregate particles are known to persons skilled in the art. An example of such a procedure is described by Scherzer (Octane-Enhancing Zeolitic FCC Catalyst, Julius Scherzer, Marcel Dekker, Inc. New York, 1990). The fluidizible silica-bound aggregate particles, like the silica bound extrudates described above, would then undergo the final step described below to convert the silica binder to a binder zeolite.

The final step of the three step process is the conversion of the silica present in the silica-bound zeolite to zeolite binder to bind the core crystals together. The core zeolite crystals are thus held together without the use of a significant amount of non-zeolite binder. The newly-formed MFI zeolite is produced as crystals. The crystals may grow on and/or adhere to the core crystals, and may also be produced in the form of new crystals that are grown together, which are generally much smaller than the initial crystals, e.g., of sub-micron size. These newly formed crystals may grow together and interconnect.

The zeolite bond zeolite may be further ion exchanged as is known in the art either to replace at least in part the original metals present in the zeolite with a different cation, e.g. a Group IB to VIII of the Periodic Table metal such as nickel, copper, zinc, calcium or rare earth metals, or to provide a more acidic form of the zeolite by exchange of alkali metal with intermediate ammonium cation followed by calcination of the ammonium form to provide the acidic hydrogen form. The acidic form may be readily prepared by ion exchange using a suitable reagent such as ammonium nitrate solution followed by calcination to remove ammonia and form the acidic hydrogen form. Ion exchange is preferably conducted after formation of the coated zeolite catalyst. Particularly preferred cations are those which render the material catalytically active, especially for certain hydrocarbon conversion reactions. These include hydrogen, rare earth metals, and one or more metals of Groups IIA, IIIA, IVA, VA, VIA, VIIA, VIII, IB, IIB, IIIB, IVB, and VB of the Periodic Table of the Elements. Examples of suitable metals include Group VIII metals (i.e., Pt. Pd, Ir, Rh, Os, Ru, Ni, Co and Fe), Group IVA metals (i.e., Sn and Pb), Group VB metals (i.e., Sb and Bi), and Group VIIB metals (i.e., Mn, Tc and Re). Noble metals (i.e., Pt, Pd, Ir, Rh, Os and Ru) are sometimes preferred. Reference to the metal is intended to encompass such metal or metals in the elemental state (i.e., zero valent) or some other catalytically active form such as an oxide, sulfide, halide, carboxylate, and the like.

The zeolite bound zeolites of the present invention can be used in processing hydrocarbonaceous feedstocks. Hydrocarbonaceous feed-stocks contain carbon compounds and can be from many different sources, such as virgin petroleum fractions, recycle petroleum fractions, tar sand oil, and, in general, can be any carbon containing fluid susceptible to zeolitic catalytic reactions. Depending on the type of processing the hydrocarbonaceous feed is to undergo, the feed can contain metal or can be free of metals. Also, the feed it can also have high or low nitrogen or sulfur impurities.

The zeolite bound zeolite by itself or in combination with one or more catalytically active substances can be used as catalysts for a variety of organic, e.g., hydrocarbon compound conversion processes. Examples of such processes include, as non-limiting examples, the following:

(A) The catalytic cracking of a naphtha feed to produce light olefins. Typical reaction conditions include from about 500° C. to about 750° C., pressures of subatmospheric or atmospheric, generally ranging up to about 10 atmospheres (gauge) and residence time (volume of the catalyst ? feed rate from about 10 milliseconds to about 10 seconds.

-continued (B) The catalytic cracking of high molecular weight hydrocarbons to lower weight hydrocarbons. Typical reaction conditions for catalytic cracking include temperatures of from about 400° C. to about 700° C., pressures of from about 0.1 atmosphere (bar) to about 30 atmospheres, and weight hourly space velocities of from about 0.1 to about 100.

(C) The transalkylation of aromatic hydrocarbons in the presence of polyalkylaromatic hydrocarbons. Typical reaction conditions include a temperature of from about 200° C. to about 500° C., a pressure of from about atmospheric to about 200 atmospheres, a weight hourly space velocity of from about 1 to about 1000 and an aromatic hydrocarbon/polyalkylaromatic hydrocarbon mole ratio of from about 1/1 to about 16/1.

(D) The isomerization of aromatic (e.g., xylene) feedstock components. Typical reaction conditions for such include a temperature of from about 230° C. to about 510° C., a pressure of from about 0.5 atmospheres to about 50 atmospheres, a weight hourly space velocity of from about 0.1 to about 200 and a hydrogen/hydrocarbon mole ratio of from about 0 to about 100.

(E) The dewaxing of hydrocarbons by selectively removing straight chain paraffins. The reaction conditions are dependent in large measure on the feed used and upon the desired pour point. Typical reaction conditions include a temperature between about 200° C. and 450° C., a pressure up to 3,000 psig and a liquid hourly space velocity from 0.1 to 20.

(F) The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about atmospheric to about 200 atmospheres, a weight hourly space velocity of from about 1 $hr^{-1}$ to about 2,000 $hr^{-1}$ and an aromatic hydrocarbon/alkylating agent mole ratio of from about 1/1 to about 20/1.

(G) The alkylation of aromatic hydrocarbons, e.g., benzene, with long chain olefins, e.g., $C_{14}$ olefin. Typical reaction conditions include a temperature of from about 50° C. to about 200° C., a pressure of from about atmospheric to about 200 atmospheres, a weight hourly space velocity of from about 2 $hr^{-1}$ to about 2000 $hr^{-1}$ and an aromatic hydrocarbon/olefin mole ratio of from about 1/1 to about 20/1. The resulting product from the reaction are long chain alkyl aromatics which when subsequently sulfonated have particular application as synthetic detergents;

(H) The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 1 to about 30 atmospheres, and an aromatic hydrocarbon weight hourly space velocity (WHSV) of from 1 $hr^{-1}$ to about 50 $hr^{-1}$;

(I) The hydrocracking of heavy petroleum feedstocks, cyclic stocks, and other hydrocrack charge stocks. The zeolite bound zeolite catalyst will contain an effective amount of at least one hydrogenation component of the type employed in hydrocracking catalysts.

(J) The alkylation of a reformate containing substantial quantities of benzene and toluene with fuel gas containing short chain olefins (e.g., ethylene and propylene) to produce mono- and dialkylates. Typical reaction conditions include temperatures from about 100° C. to about 250° C., a pressure of from about 100 to about 800 psig, a WHSV -olefin from about 0.4 $hr^{-1}$ to about 0.8 $hr^{-1}$, a WHSV -reformate of from about 1 $hr^{-1}$ to about 2 $hr^{-1}$ and, optionally, a gas recycle from about 1.5 to 2.5 vol/vol fuel gas feed.

(K) The alkylation of aromatic hydrocarbons, e.g., benzene, toluene, xylene, and naphthalene, with long chain olefins, e.g., $C_{14}$ olefin, to produce alkylated aromatic lube base stocks. Typical reaction conditions include temperatures from about 160° C. to about 260° C. and pressures from about 350 to 450 psig.

(L) The alkylation of phenols with olefins or equivalent alcohols to provide long chain alkyl phenols. Typical reaction conditions include temperatures from about 100° C. to about 250° C., pressures from about 1 to 300 psig and total WHSV of from about 2 $hr^{-1}$ to about 10 $hr^{-1}$.

(M) The conversion of light paraffins to olefins and/or aromatics.

-continued

Typical reaction conditions include temperatures from about 425° C. to about 760° C. and pressures from about 10 to about 2000 psig.

(N) The conversion of light olefins to gasoline, distillate and lube range hydrocarbons. Typical reaction conditions include temperatures of from about 175° C. to about 375° C. and a pressure of from about 100 to about 2000 psig.

(O) Two-stage hydrocracking for upgrading hydrocarbon streams having initial boiling points above about 200° C. to premium distillate and gasoline boiling range products or as feed to further fuels or chemicals processing steps in a first stage using in the first stage the zeolite bound zeolite catalyst comprising one or more catalytically active substances, e.g., a Group VIII metal, and the effluent from the first stage would be reacted in a second stage using a second zeolite, e.g., zeolite Beta, comprising one or more catalytically active substances, e.g., a Group VIII metal, as the catalyst. Typical reaction conditions include temperatures from about 315° C. to about 455° C., a pressure from about 400 to about 2500 psig, hydrogen circulation of from about 1000 to about 10,000 SCF/bbl and a liquid hourly space velocity (LHSV) of from about 0.1 to 10;

(P) A combination hydrocracking/dewaxing process in the presence of the zeolite bound zeolite catalyst comprising a hydrogenation component and zeolite Beta. Typical reaction conditions including temperatures from about 350° C. to about 400° C., pressures from about 1400 to about 1500 psig, LHSVs from about 0.4 to about 0.6 and a hydrogen circulation from about 3000 to about 5000 SCF/bbl.

(Q) The reaction of alcohols with olefins to provide mixed ethers, e.g., the reaction of methanol with isobutene and/or isopentene to provide methyl-t-butyl ether (MTBE) and/or t-amyl methyl ether (TAME). Typical conversion conditions including temperatures from about 20° C. to about 200° C., pressures from 2 to about 200 atm, WHSV (gram-olefin per hour gram-zeolite) from about 0.1 $hr^{-1}$ to about 200 $hr^{-1}$ and an alcohol to olefin molar feed ratio from about 0.1/1 to about 5/1.

(R) The disproportionation of toluene to make benzene and paraxylene. Typical reaction conditions including a temperature of from about 200° C. to about 760° C., a pressure of from about atmospheric to about 60 atmosphere (bar), and a WHSV of from about 0.1 $hr^{-1}$ to about 30 $hr^{-1}$.

(S) The conversion of naphtha (e.g. $C_6$—$C_{10}$) and similar mixtures to highly aromatic mixtures. Thus, normal and slightly branched chained hydrocarbons, preferably having a boiling range above about 40° C., and less than about 200° C., can be converted to products having a substantial higher octane aromatics content by contacting the hydrocarbon feed with the zeolite at a temperature in the range of from about 400° C. to 600° C., preferably 480° C. to 550° C. at pressures ranging from atmospheric to 40 bar, and liquid hourly space velocities (LHSV) ranging from 0.1 to 15.

(T) The absorption of alkyl aromatic compounds for the purpose of separating various isomers of the compounds.

(U) The conversion of oxygenates, e.g., alcohols, such as methanol, or ethers, such as dimethylether, or mixtures thereof to hydrocarbons including olefins and aromatics with reaction conditions including a temperature of from about 275° C. to about 600° C., a pressure of from about 0.5 atmosphere to about 50 atmospheres and a liquid hourly space velocity of from about 0.1 to about 100;

(V) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous state phase with a zeolite bound zeolite at a temperature in the range of from about 250° C. to about 800° C., a LHSV of from about 0.2 to about 50 and a hydrocarbon partial pressure of from about 0.1 to about 50 atmospheres. Temperatures below about 250° C. may be used to oligomerize the feedstock when the feedstock is in the liquid phase when contacting the zeolite bound zeolite catalyst. Thus, when the olefin feedstock contacts the catalyst in the liquid phase, temperatures of from about 10° C. to about 250° C. may be used.

(W) The conversion of $C_2$ unsaturated hydrocarbons (ethylene and/or acetylene) to aliphatic $C_{6-12}$ aldehydes and converting said aldehydes to the corresponding $C_{6-12}$ alcohols, acids, or esters.

In general, therefore, catalytic conversion conditions over a catalyst comprising the zeolite bound zeolite include a temperature of from about 100° C. to about 760° C., a pressure of from about 0.1 atmosphere (bar) to about 200 atmospheres (bar), a weight hourly space velocity of from about 0.08 $hr^{-1}$ to about 2,000 $hr^{-1}$.

The zeolite-bound zeolite of the present invention has particular application in the vapor phase disproportionation of toluene. Such vapor phase disproportionation comprises contacting toluene under disproportionation conditions with the zeolite bound zeolite catalyst to yield a product mixture which comprises a mixture of unreacted (unconverted) toluene, benzene and xylene. In the more preferred embodiment, the catalyst is first selectivated prior to use in the disproportionation process to enhance conversion of toluene to xylene and to maximize the catalyst selectivity towards the production of paraxylene. Selectivation of the catalyst can be accomplished by depositing coke on the catalyst surface or by treating the catalyst with a selectivation agent such as an organosilicon compound. Disproportionation conditions include a temperature between about 400° C. and 550° C., more preferably between about 425° C. and 510° C., at a hydrogen to toluene mole ratio of from 0 to about 10, preferably between about 0.1 and 5 and more preferably from about 0.1 to less than 1, at a pressure between about 1 atmosphere and 100 atmospheres and utilizing WHSV of between about 0.5 and 50.

The zeolite bound zeolite of the present invention is also especially useful as a catalyst in a process for isomerizing one or more xylene isomers in a $C_8$ aromatic feed to obtain ortho-, meta-, and para-xylene in a ratio approaching the equilibrium value. It is important that xylene isomerization catalysts produce a near equilibrium mixture of xylenes and it is also sometimes desirable that the catalysts convert ethylbenzene with very little net loss of xylenes.

In the vapor phase, suitable isomerization conditions include a temperature in the range 250° C.–600° C., preferably 300° C.–550° C., a pressure in the range 0.5–50 atm abs, preferably 10–25 atm abs, and a weight hourly space velocity (WHSV) of 0.1 to 100, preferably 0.5 to 50. Optionally, isomerization in the vapor phase is conducted in the presence of 3.0 to 30.0 moles of hydrogen per mole of alkylbenzene. If hydrogen is used, the catalyst should comprise 0.1 to 2.0 wt % of a hydrogenation/dehydrogenation component selected from Group VIII of the Periodic Table, especially platinum, palladium, or nickel.

The zeolite bound zeolite of the present invention are especially useful as a catalyst in a process for cracking a $C_4^+$ naphtha feed, particularly a $C_4$ 290° C. naphtha feed to produce low molecular weight olefins, e.g., $C_2$ through $C_4$ olefins, particularly ethylene and propylene. Such a process is preferably carried out by contacting the naphtha feed at temperatures ranging from 500° C. to about 750° C., more preferably 550° C. to 675° C., at a pressure from subatmospheric up to 10 atmospheres, but preferably from about 1 atmosphere to about 3 atmospheres.

The zeolite bound zeolite of the present invention are especially useful as a catalyst in the transalkylation of polyalkylaromatic hydrocarbons. Examples of suitable polyalkylearomatic hydrocarbons include di-, tri-, and tetra-alkyl aromatic hydrocarbons, such as diethylbenzene, triethylbenzene, diethylmethylbenzene (diethyltoluene), diisopropyl-benzene, triisopropylbenzene, diisopropyltoluene, dibutylbenzene, and the like. Preferred polyalkylaromatic hydrocarbons are the dialkyl benzenes. Particularly preferred polyalkylaromatic hydrocarbons are diisopropylbenzene and diethylbenzene.

The transalkylation process will preferably have a molar ratio of aromatic hydrocarbon to polyalkylaromatic hydrocarbon of preferably from about 0.5:1 to about 50:1, and more preferably from about 2:1 to about 20:1. The reaction temperature will preferably range from about 340° C. to 500° C. to maintain at least a partial liquid phase, and the pressure will be preferably in the range of about 50 psig to 1,000 psig, preferably 300 psig to 600 psig. The weight hourly space velocity will range from about 0.1 to 10.

The following example illustrates a process for the preparation of a zeolite bound zeolite catalyst of the present invention.

EXAMPLE 1

Preparation of TON Structure Type Zeolite Bound by MFI Structure Type Zeolite using Seed Crystals TON structure type zeolite crystals were formed into TON structure type zeolite bound with silica containing seed crystals as follows:

| Components Used for Preparation | Quantity, (Grams) | Component No. |
|---|---|---|
| Zeolite H-ZSM-22 Crystals | 100.02 | 1 |
| Water | 200.00 | 2 |
| Colloidal seed suspension (31.7 wt % colloidal silicalite with a particle size of ~80 nm) | 0.35 | 3 |
| Aerosil 300 | 9.58 | 4 |
| Nyacol 2034 DI (34% SiO$_2$) | 98.68 | 5 |
| Methocel extrusion aid | 1.86 | 6 |

Components 1 and 2 were mixed in the bowl of a household mixer. Next, component 3 was added to the bowl and the contents were mixed. Next, component 4 was added to the bowl and the contents were mixed. Component 5 was then added to the bowl and the mixing continued. Total mixing time was about 38 minutes. A plastic extrudable dough was obtained. The dough was extruded into 2 mm extrudates. The extrudates were dried overnight at 120° C. and then calcined for 7.0 hours at 500° C. in air. The extrudates contained 30.35 weight percent silica.

The extrudates of TON structure type zeolite bound with silica containing colloidal silicalite seeds were converted into TON structure type zeolite bound by MFI structure type zeolite as follows:

| Components used For Preparation | Quantity, (Grams) | Component No. |
|---|---|---|
| NaOH (98.6%) | 1.04 | 1 |
| Al(OH)$_3$(98.5%) | 0.69 | 2 |
| Water | 20.03 | 3 |
| Rinse Water | 14.12 | 4 |
| TPABr (>98%) | 3.60 | 5 |
| H$_2$O | 26.05 | 6 |
| Rinse Water | 3.99 | 7 |

-continued

| Components used For Preparation | Quantity, (Grams) | Component No. |
|---|---|---|
| H-ZSM-22 Bound by Silica Containing Colloidal Silicalite Seeds | 30.00 | 8 |

Components 1 and 2 were dissolved into component 3 by boiling to form a solution. In order to correct for water loss due to boiling, water was added to achieve a total weight of 21.76 grams. In a separate container, component 5 was dissolved into component 6. The two solutions were transferred to a 300 ml stainless steel autoclave, using components 4 and 7 to quantitatively transfer the solutions. Finally component 8 was then added to the autoclave. The molar composition of the synthesis mixture was:

0.85 Na$_2$O/0.90 TPABr/0.290 Al$_2$O$_3$/10 SiO$_2$/239 H$_2$O

The autoclave was placed into a room temperature oven and the oven was heated to 150° C. within 2 hours. After 80 hours of heating at that temperature, crystallization was stopped. The product extrudates were washed 6 times with 900 ml water at 60° C. The conductivity of the last wash water was 45 $\mu$S/cm. The product was dried in an oven for 7 hours at 150° C. The amount of product recovered after drying was 33.06 gr.

Characterization of the product extrudates by x-ray diffraction (XRD) showed excellent crystallinity and conversion of the silica into MFI structure type zeolite. No amorphous halo could be seen, which would have indicated the presence of unconverted silica.

COMPARATIVE EXAMPLE A

Preparation of TON Structure Type Zeolite Bound by MFI Structure Type Zeolite without using Seed Crystals TON structure type zeolite crystals were formed into TON structure type zeolite bound by silica without seed crystals being present as follows:

| Components Used for Preparation | Quantity, (Grams) | Component No. |
|---|---|---|
| Zeolite H-ZSM-22 Crystals | 100.02 | 1 |
| Water | 200.00 | 2 |
| Aerosil 300 | 9.58 | 3 |
| Nyacol 2034 DI (34% SiO$_2$) | 98.68 | 4 |
| Methocel extrusion aid | 1.86 | 5 |

Components 1 and 2 were mixed in the bowl of a household mixer. Next, component 3 was added to the bowl and the contents were mixed. Component 4 was then added to the bowl and the mixing continued. Total mixing time was about 30 minutes. A plastic extrudable dough was obtained. The dough was extruded into 2 mm extrudates. The extrudates were dried overnight at 120° C. and then calcined for 7.0 hours at 500° C. in air. The extrudates contained 30.35 weight percent silica.

Conversion of the silica-bound TON structure type zeolite extrudates into TON structure type zeolite bound by MFI structure type zeolite was carried out as follows:

| Components used for Preparation | Quantity, (Grams) | Component No. |
| --- | --- | --- |
| NaOH (98.6%) | 0.94 | 1 |
| Al (OH)$_3$(98.5%) | 0.69 | 2 |
| Water | 19.86 | 3 |
| Rinse Water | 14.12 | 4 |
| TPABr (>98%) | 3.60 | 5 |
| H$_2$O | 26.05 | 6 |
| Rinse Water | 3.99 | 7 |
| H-ZSM-22 Bound by Silica Containing No Colloidal Silicalite Seeds | 30.00 | 8 |

Components 1 and 2 were dissolved into component 3 by boiling to form a solution. In order to correct for water loss due to boiling, water was added to achieve a total weight of 21.49 grams. In a separate container, component 5 was dissolved into component 6. The two solutions were transferred to a 300 ml stainless steel autoclave, using components 4 and 7 to quantitatively transfer the solutions. Finally component 8 was then added to the autoclave. The molar composition of the synthesis mixture was:

0.80 Na$_2$O/0.90 TPABr/0.290 Al$_2$O$_3$/10 SiO$_2$/237 H$_2$O

The autoclave was placed into a room temperature oven and the oven was heated to 150° C. within 2 hours. After 72 hours of heating at that temperature, crystallization was stopped. The product extrudates were washed 6 times with 900 ml water at 60° C. The product was dried in an oven for 7 hours at 150° C.

Characterization of the product extrudates by x-ray diffraction (XRD) showed that, in comparison to the product of Example 1, substantially less silica binder was converted into ZSM-5.

COMPARATIVE EXAMPLE B

Preparation of TON Structure Type Zeolite Bound by MFI Structure Type Zeolite without using Seed Crystals Silica-bound TON structure type zeolite crystals were converted into TON structure type zeolite bound by MFI structure type crystals as follows:

| Component | Ingredients | Quantity in Grams |
| --- | --- | --- |
| A | NaOH (98.6%%) | 2.03 |
|   | Al(OH)$_3$ (98.5%) | 1.15 |
|   | H$_2$O | 25.01 |
| B | TPABr | 6.03 |
|   | H$_2$O | 16.80 |
| C | Silica bound ZSM-22 | 50.04 |
| D | Rinse Water | 52.17 |
| E | Rinse Water | 11.70 |

A and B were prepared using the same procedures as described in Example 3. Next, the synthesis liquor was formed using the same procedure as described in Example 3. The synthesis liquor had the following composition:

1.00 Na$_2$O/0.91 TPABr/0.291 Al$_2$O$_3$/10 SiO$_2$/236 H$_2$O

OH—/SiO$_2$=0.20

SiO$_2$/Al$_2$O$_3$=34.4

The synthesis liquor was transferred to a stainless steel autoclave and heated to 150° C. in 2 hours and heating was continued at this temperature for 64 hours. The resulting product was then washed and dried.

Characterization of the product by x-ray diffraction showed that the product was a mixture of ZSM-5 and ZSM-22 with conversion of the silica to MFI being substantially complete. However, the resulting extrudates did not have good physical strength as they fell apart.

EXAMPLE 2

Preparation of TON Structure Type Zeolite Bound by MFI Structure Type Zeolite using Seed Crystals

A.

Silica-bound TON structure type zeolite crystals were converted into TON structure type zeolite bound by MFI structure type crystals as follows:

| Component | Ingredients | Quantity in Grams |
| --- | --- | --- |
| A | NaOH (98.6%%) | 0.311 |
|   | Al(OH)$_3$ (98.5%) | 0.131 |
|   | H$_2$O | 10.02 |
| B | TPABr | 1.82 |
|   | H$_2$O | 10.03 |
| C | Silica bound ZSM-22 containing 0.077 wt. % colloidal seed crystals | 15.0 |
| D | Rinse Water | 5.11 |
| E | Rinse Water | 6.70 |

A was prepared by combining the ingredients and was boiled until a clear solution was obtained. The solution was cooled to room temperature and water was added to compensate for the water loss during the boiling. B was prepared at room temperature. A and B were poured into a 150 ml stainless steel autoclave using rinse water D and E to ensure complete transfer of A and B. C was then added. The extrudates were just covered with synthesis liquor.

The synthesis liquor had the following molar composition:

0.51 Na$_2$O/0.91TPABr/0.111 Al$_2$O$_3$/10 SiO$_2$/240 H$_2$O

OH/SiO$_2$=0.1

The autoclave was heated to 150° C. in 2 hours and heating was continued for 48 hours at this temperature. The product was then washed and dried.

Characterization of the product extrudates by x-ray diffraction showed that the product consisted mainly of ZSM-5 and ZSM-22.

B.

The preparation of ZSM-22 bound by ZSM-5 was repeated using the same procedures except that the heating time in the autoclave was reduced to 19 hours.

Characterization of the product extrudates by x-ray diffraction (XRD) showed that the product was a mixture of binder ZSM-5 with ZSM-22. The ratio of ZSM-5 to ZSM-22 was less than the product of A above.

What is claimed is:

1. A process for preparing a zeolite bound zeolite which does not contain significant amounts of non-zeolitic binder, which process comprises:

aging a silica-bound aggregate containing zeolite other than MFI structure type zeolite and an amount of seed crystals of MFI structure type which were added to the mixture used to form the silica-bound aggregate in an aqueous ionic solution containing a sufficient amount of hydroxy ions to convert the silica binder to the MFI structure type binder and optionally a template.

2. The process recited in claim 1 wherein the amount of seed crystals present is from about 0.01 to about 2.0 weight percent based on the dry weight of the silica bound extrudate.

3. The process recited in claim 2 wherein said seed crystals have an average diameter of 200 nm or less.

4. The process recited in claim 2 wherein the conversion is carried out at a temperature in the range of from about 130° C. to 170° C.

5. The process recited in claim 2 wherein said zeolite other than MFI structure type zeolite has pore apertures consisting of about 8 to about 10 membered ring structures.

6. The process recited in claim 2 wherein said (OH$^-$):(SiO$_2$) molar ratio is less than about 0.16.

7. The process recited in claim 2 wherein the silica bound aggregate is aged for a period of from about 10 to about 80 hours.

8. The process recited in claim 2 wherein said zeolite other than MFI structure type zeolite has a TON structure type.

9. The process recited in claim 2, wherein said seed crystals have an average diameter of 100 nm or less and are capable of forming a colloidal suspension.

10. The process recited in claim 9 wherein said zeolite other than MFI structure type zeolite has a composition with the following molar relationship:

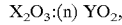

$$X_2O_3:(n)\ YO_2,$$

wherein X is aluminum, boron, iron, and/or gallium, Y is silicon, tin, and/or germanium, and n has a value of at least 2.

11. The process recited in claim 2, wherein said zeolite other than MFI structure type zeolite has lower acidity than the MFI binder zeolite.

12. The process recited in claim 11, wherein said zeolite other than MFI structure type zeolite is an intermediate pore size zeolite.

13. The process recited in claim 2, wherein said zeolite other than MFI structure type zeolite and the MFI structure zeolite are an aluminosilicate zeolite or a gallium silicate zeolite.

14. The process recited in claim 2 wherein said seed crystals are silicalite.

15. The process recited in claim 2 wherein said MFI binder zeolite has a silica to alumina mole ratio of less than 100.

16. The process recited in claim 2 wherein said zeolite bound zeolite contains less than 5% by weight of non-zeolitic binder.

17. The process recited in claim 2 wherein said aqueous ionic solution contains a template.

18. The process recited in claim 2 wherein the binder zeolite has higher acidity than the zeolite in the aggregate.

19. The process recited in claim 2 wherein said process is carried out by the following steps:

(a) Forming an extrudable mass comprising core crystals of a zeolite other than MFI, silica, water, an amount of seeds of MFI structure type zeolite, and optionally an extrusion aid;

(b) Extruding the extrudable mass to form silica-bound zeolite aggregates; and (c) Aging the silica bound zeolite aggregate in an aqueous ionic solution containing sufficient hydroxy ions and optionally an organic template at sufficient temperature to cause the silica binder to be converted to the MFI binder crystals.

20. The process recited in claim 19 wherein the binder crystals are intergrown and form at least a partial coating on the crystals of said zeolite other than MFI structure type zeolite.

21. The process cited in claim 20 wherein the crystals of said zeolite other than MFI structure type zeolite have an average particle size of from about 1 to about 15 microns and the MFI binder crystals have an average particle size of from about 0.1 to about 0.5 micron.

* * * * *